United States Patent
Boyle

(10) Patent No.: US 9,981,893 B2
(45) Date of Patent: May 29, 2018

(54) METHOD TO SYNTHESIZE LANTHANIDE FLUORIDE MATERIALS FROM LANTHANIDE FLUORINATED ALKOXIDES

(71) Applicant: National Technology & Engineering Solutions of Sandia, LLC, Albuquerque, NM (US)

(72) Inventor: Timothy J. Boyle, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 70 days.

(21) Appl. No.: 15/010,899

(22) Filed: Jan. 29, 2016

(65) Prior Publication Data
US 2016/0229773 A1    Aug. 11, 2016

Related U.S. Application Data

(60) Provisional application No. 62/112,286, filed on Feb. 5, 2015.

(51) Int. Cl.
*A61K 51/00* (2006.01)
*A61M 36/14* (2006.01)
*C07C 29/70* (2006.01)
*C07C 29/00* (2006.01)
*C01F 17/00* (2006.01)

(52) U.S. Cl.
CPC .......... *C07C 29/70* (2013.01); *C01F 17/0062* (2013.01); *C01P 2004/64* (2013.01); *C07C 29/00* (2013.01)

(58) Field of Classification Search
None
See application file for complete search history.

(56) References Cited

PUBLICATIONS

Bradley et al. (Polyhedron) 1992, 11, 375-379).*
Hernandez-Sanchez et al. (IEEE Trans. Nanobiosci. 2006, 5, 222-230).*
Pratt, Sarah Hoppe, et al. Synthesis and characterization of a novel family of yttrium alkoxides for production of luminescent nanomaterials. No. SAND2011-6125C. Sandia National Laboratories (SNL-NM), Albuquerque, NM (United States), 2011.*
Bradley, D.C. Alkoxo and Aryloxo Derivatives of Metals, Academic Press 2001, p. 41-43.*
Boyle, T.J. et al., "Advances in structurally characterized lanthanide alkoxide, aryloxide, and silyloxide compounds", Chem. Rev. 108 (6) (2008), pp. 1896-1917.
Sorokin, N.I. et al., "Nonstoichiometric Fluorides—Solid Electrolytes for Electrochemical Devices: A Review", Crystallography Reports, vol. 52, No. 5 (2007), pp. 842-863.
Bralic, M. et al., "Fluoride electrode with LaF3-membrahe and simple disjoining solid-state internal contact", Talanta 55 (2001), pp. 581-586.

* cited by examiner

*Primary Examiner* — Michael G Hartley
*Assistant Examiner* — Melissa J Perreira
(74) *Attorney, Agent, or Firm* — Kevin W. Bieg

(57) ABSTRACT

Lanthanide fluorinated alkoxide derivatives can be synthesized from the alcoholysis reaction of the lanthanide bis-trimethylsilyl amide and an excess amount of hexafluoro iso-propanol. Nanoparticles can be formed from the lanthanide fluorinated alkoxide derivatives by a solvothermal or solution precipitation process.

14 Claims, 4 Drawing Sheets

METHOD TO SYNTHESIZE LANTHANIDE FLUORIDE MATERIALS FROM LANTHANIDE FLUORINATED ALKOXIDES

CROSS-REFERENCE TO RELATED APPLICATION

This application claims the benefit of U.S. Provisional Application No. 62/112,286, filed Feb. 5, 2015, which is incorporated herein by reference.

STATEMENT OF GOVERNMENT INTEREST

This invention was made with Government support under contract no. DE-AC04-94AL85000 awarded by the U. S. Department of Energy to Sandia Corporation. The Government has certain rights in the invention.

FIELD OF THE INVENTION

The present invention relates to lanthanide fluoride materials and, in particular, to a method to synthesize lanthanide fluoride materials from lanthanide fluorinated alkoxides for renewable geothermal power and other applications.

BACKGROUND OF THE INVENTION

Since the first successful demonstration of electricity generated from geothermal sources in 1904 in Larderllo, Italy (four lightbulbs were illuminated), the exploitation of renewable geothermal power (GTP) has continued to grow around the world. Currently more than 25 countries rely on some form of GTP for production of electricity, with the largest output coming from "The Geysers" in Santa Rosa Calif., USA. In an ideal situation, the subsurface fluid (4 km underground at greater than 100° C.) is pumped to the surface and the hot liquid is used to turn a steam turbine to generate electricity (i.e., a steam turbine system), returned underground by another well, geothermally re-heated, and the process started again. While GTP is a simple, cost effective, and 'green' method to produce self-reliant electricity, the number of acceptable, naturally occurring sites that can profitably generate electricity is limited. Therefore, interest has focused on using 'hot rock' sub-stratus to heat injected water (i.e., generate a heated aquifer). To maintain a 'closed' system, the rock between the two well bores must be explosively fractured. For both of these systems, the characterization of the reservoir fracture networks is important in the successful development GTP.

Often ion-based tracer studies are used to elucidate the extent and connectivity of these fracture networks. However, collecting real-time down-hole tracer data requires the development of novel ion detecting sensors. These detectors must survive the extreme brine pH levels (high and low), high temperature, high pressure, and other environmental conditions encountered in these deep-hole wells. Several detectors are being pursued for this application, including fluorine ion selective electrodes. One proposed material for the electrode is $LaF_3$, which has shown some laboratory success. See N. I. Sorokin and B. P. Sobolev, *Cryst. Reports*, 842 (2007); and M. Bralic et al., *Talanta*, 581 (2001). However, a need remains for an improved method to synthesize $LaF_3$ nanomaterials having increased detection capability.

SUMMARY OF THE INVENTION

The present invention is directed to the synthesis of a series of lanthanide fluorinated alkoxide derivatives from the alcoholysis reaction of the lanthanide bis-trimethylsilyl amide dissolved in an organic solvent and an excess amount of hexafluoro iso-propanol (H-hfip). The products from this reaction were isolated and identified by single crystal X-ray diffraction as: [cis-$(H_2O)_2$(hfip)$_2$Ln($\mu$-hfip)]$_2$ (Ln=Ce, Pr, Nd, Sm, Eu, Gd, Tb, Dy, Ho, Er, Tm, Yb, Lu, and Y), [trans-$(H_2O)_2$(hfip)$_2$Sc($\mu$-hfip)]$_2$ (Sc), [$(H_2O)_2$(hfip)$_2$La$_2$($\mu$-hfip)$_3$ ($\mu_3$-OH)]$_2$ (La—OH), and [$(H_2O)$(hfip)$_2$Sc($\mu$-hfip)($\mu$-OH)($\mu_3$-OH)Sc$(H_2O)$(hfip)]$_2$(Sc—OH). The invention is further directed to the generation of $LnF_3$ nanomaterials from the lanthanide fluorinated alkoxide derivatives by solvothermal (SOLVO) or solution precipitation (SPPT) routes.

BRIEF DESCRIPTION OF THE DRAWINGS

The detailed description will refer to the following drawings, wherein like elements are referred to by like numbers.

DETAILED DESCRIPTION OF THE INVENTION

Figure 1:
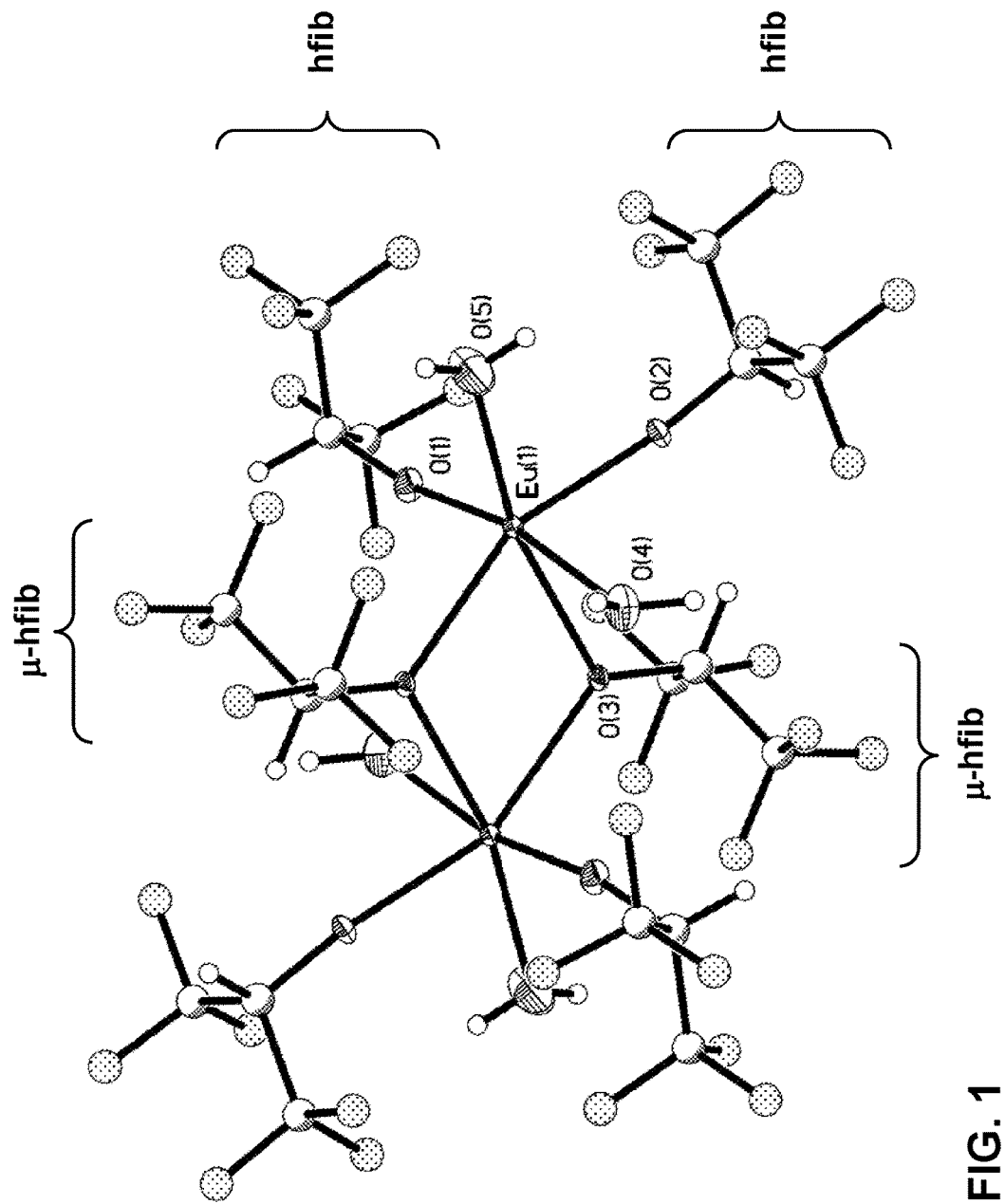
FIG. 1 is a structure plot of [cis-$(H_2O)_2$(hfip)$_2$Eu($\mu$-hfip)]$_2$. Thermal ellipsoids of heavy atoms are drawn at 30%. Carbon, fluorine (dotted) and hydrogen atoms are drawn as ball and stick for clarity.

While bulk $LnF_3$ is commercially available, nanomaterials are of interest due to their high surface area and supposed increased detection ability. The present invention is directed to the synthesis of a series of lanthanide hexafluoro iso-propoxide ($[Ln(hfip)_3]_n$) derivatives and their use in conversion to the desired $LnF_3$ nanomaterials. The $[Ln(hfip)_3]$ species are synthesized from the alcoholysis reaction of lanthanide bis-trimethylsilyl amide $[Ln(NR_2)_3]_n$, where R=Si(CH$_3$)$_3$, with an excess amount (xs) of hexafluoro iso-propanol (H-hfip, or H—OCH(CF$_3$)$_2$) in toluene, according to eq. 1:

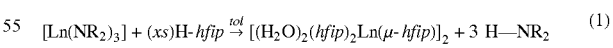

$$[Ln(NR_2)_3] + (xs)\text{H-}hfip \xrightarrow{tol} [(H_2O)_2(hfip)_2Ln(\mu\text{-}hfip)]_2 + 3\,\text{H—NR}_2 \quad (1)$$

Other non-polar organic solvents, such as hexane, can also be used. As will be described below, the products from this reaction were isolated and identified by single crystal X-ray diffraction as [cis-$(H_2O)_2$(hfip)$_2$Ln($\mu$-hfip)]$_2$(Ln=Ce, Pr, Nd, Sm, Eu, Gd, Tb, Dy, Ho, Er, Tm, Yb, Lu, and Y), [trans-$(H_2O)_2$(hfip)$_2$Sc($\mu$-hfip)]$_2$ (Sc), [$(H_2O)_2$(hfip)$_2$La$_2$($\mu$-hfip)$_3$($\mu_3$-OH)]$_2$(La—OH), and [$(H_2O)$(hfip)$_2$Sc($\mu$-hfip)($\mu$-OH)($\mu_3$-OH)Sc$(H_2O)$(hfip)]$_2$(Sc—OH). Select species from this novel family of compounds were used to characterize and survey the utility of these compounds as precursors to $LnF_3$ nanomaterials under solvothermal (SOLVO) and solution precipitation (SPPT) conditions.

All compounds described below were handled with rigorous exclusion of air and water using standard Schlenk line and glove box techniques, unless otherwise noted. All anhydrous solvents and H-hfip were used as received. The H-hfip ligand was selected from the commercially available fluorinated alcohols (versus trifluorethanol and nona-fluorobutanol) since these derivatives were found to readily generate single crystals. [Ln(NR$_2$)$_3$] was synthesized according to literature reports. See T. J. Boyle et al., "Advances in structurally characterized lanthanide alkoxide, aryloxide, and silyloxide compounds," Chem. Rev. 108 (6), 1896 (2008); and R. E. Thoma, Rare-Earth Halides; Oak Ridge National Laboratory Libraries (3 4456 0548262 5): Oak Ridge National Laboratory, May 1965; pp 1-60. Analytical data were collected on freshly dried crystalline samples. Crystals are preferred due to the limited number of analytical methods available to fully characterize these compounds due to the paramagnetic nature of the Ln cations, which limits the usefulness of NMR data, and the volatility and decomposition properties of the fluorinated ligands, which limits thermal analysis. Therefore, FTIR spectroscopy, melting point, complexometric titrations, and single crystal analyses were performed on the resulting isolated species.

Synthesis of Hfip-Ln Series Derivatives

The synthesis of the hfip-Ln series derivatives was undertaken according to eq 1. To a slurry of [Ln(NR$_2$)$_3$] in toluene in a vial, excess amounts of H-hfip were added via pipette. Upon addition of the H-hfip, the [Ln(NR$_2$)$_3$] in toluene slurry bubbled profusely, with the release of HNR$_2$. In addition, the original color associated with the [Ln(NR$_2$)$_3$] was lost upon addition of the alcohol or rendered very pale versions of the original color. The H-hfip was added until the reaction went clear. X-ray quality crystals were grown by slow evaporation of the volatile component of the reaction mixture and this typically occurred in less than 12 h. The mother liquor was removed, some crystals removed for single crystal X-ray analysis and the remainder of material was washed with hexanes, dried en vacuo, and the resulting powders were used for analyses.

Characterization

FTIR Spectroscopy.

Typically the loss of the HO— stretch for the alcohol is a convenient method for following the completion of an amide-alcohol exchange via FTIR spectroscopy. In this case, each spectrum displayed a strong HO-stretch around 3000 cm$^{-1}$. The loss of the amide stretches and ingrowth of the resonances associated with the OCH(CF$_3$)$_2$ ligand were strong indications that the reaction had proceeded according to eq. 1. The —OH stretch was originally thought to be retention of free H-hfip due to the large excess of the alcohol used in the reaction mixture. Since crystals were easily isolated, single crystal X-ray structure experiments were undertaken for each sample to assist in identifying the structure of these compounds.

X-Ray Diffraction.

The syntheses and characterization of the Ln series of hfip-modified compounds (excluding Pm but including Y and Sc) were investigated with all but Sm yielding a successful single crystal X-ray diffraction solution. These crystals were found to adopt the same general construct (except La—OH) with varied amounts of bound water.

Figure 2A:
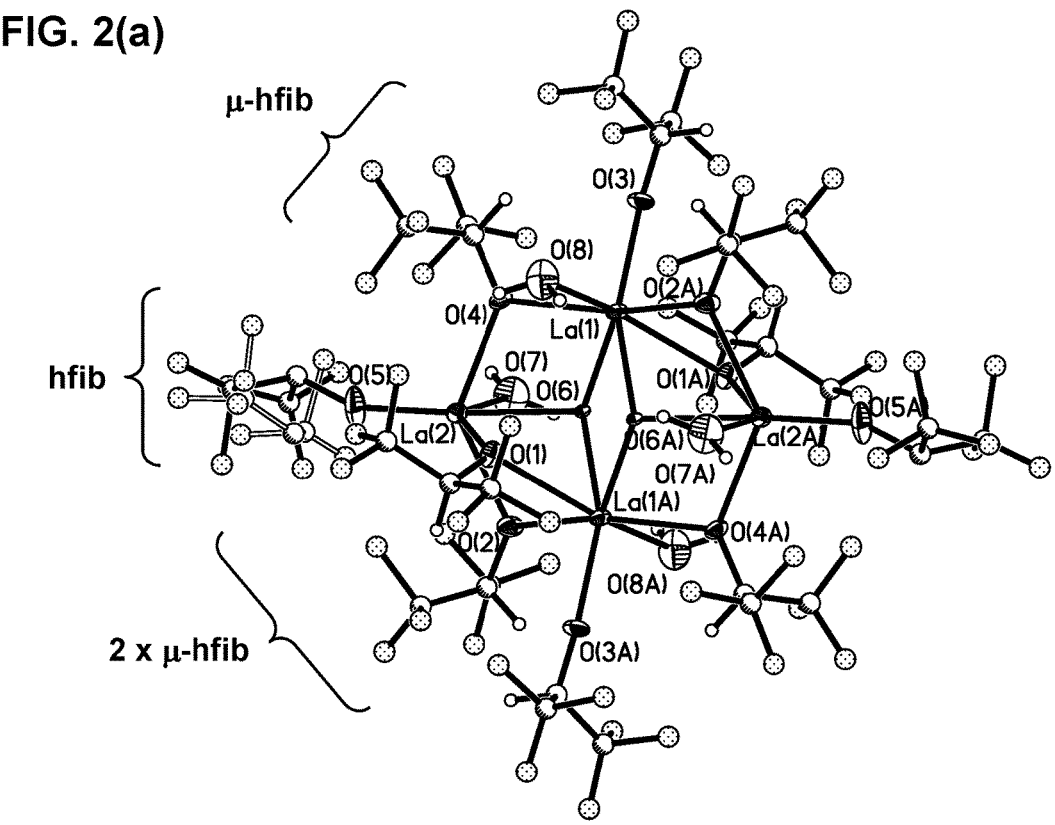
FIG. 2(a) is a structure plot of [$(H_2O)_2$(hfip)$_2$La$_2$($\mu$-hfip)$_3$($\mu_3$-OH)]$_2$.
Figure 2B:
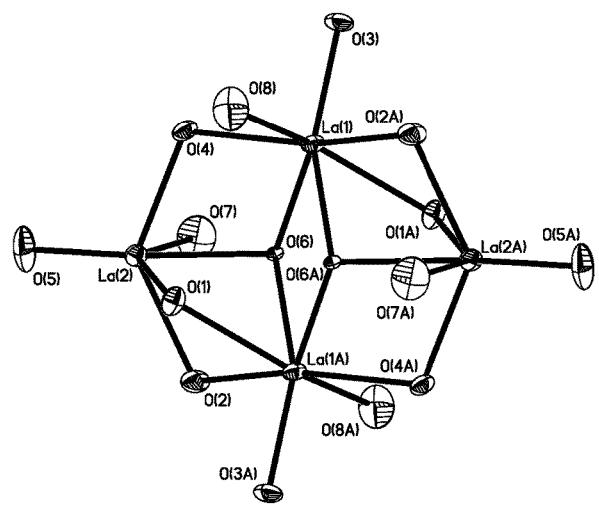
FIG. 2(b) is a structure plot of the central core. Thermal ellipsoids of heavy atoms are drawn at 30%. Carbon, fluorine (dotted) and hydrogen atoms are drawn as ball and stick for clarity.
Figure 3:
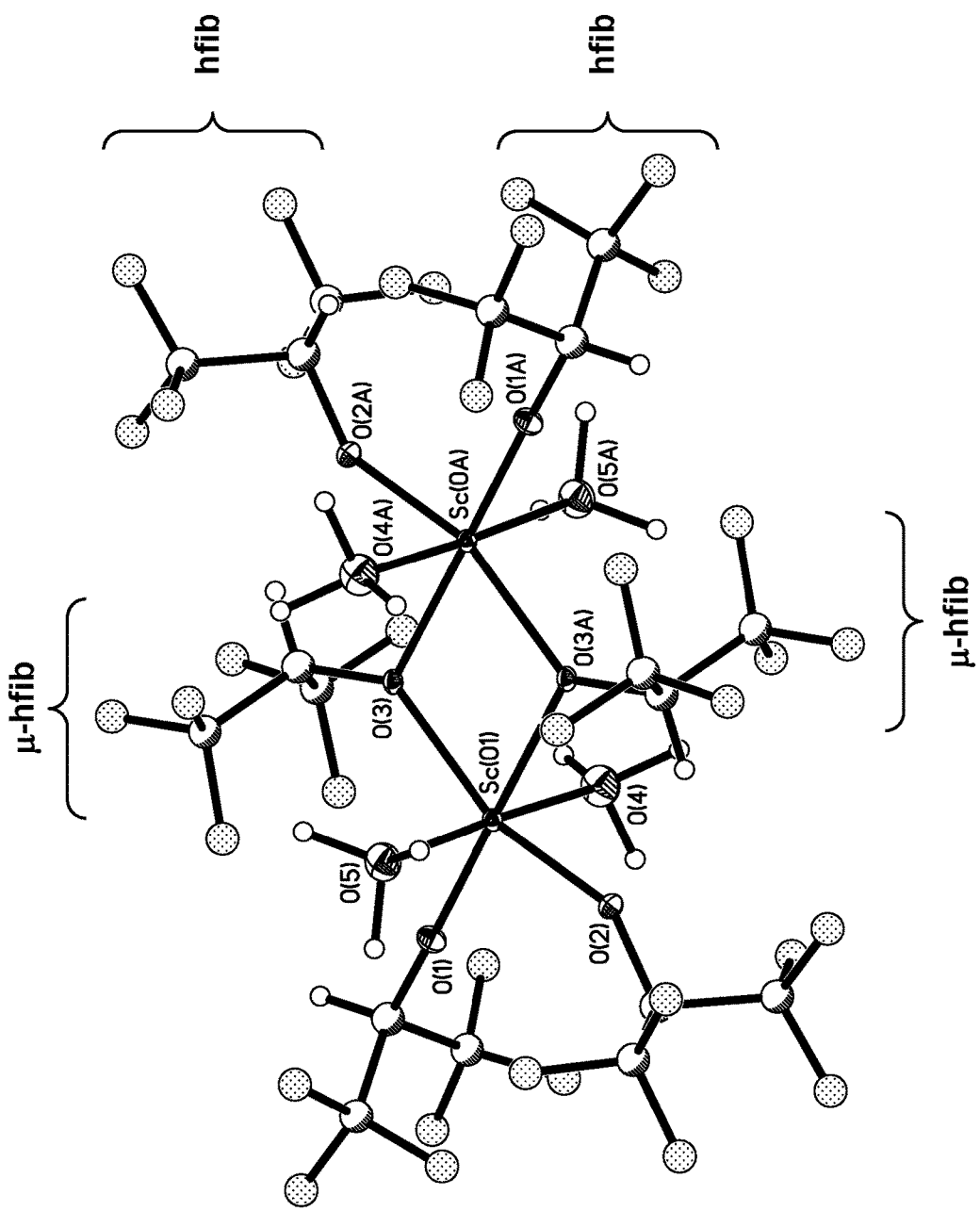
FIG. 3 is a structure plot of [trans-$(H_2O)_2$(hfip)$_2$Sc($\mu$-hfip)]$_2$. Thermal are ellipsoids of heavy atoms drawn at 30%. Carbon, fluorine (dotted) and hydrogen atoms are drawn as ball and stick for clarity.

Tables 1(a)-(c) list the data collection parameters. The entire series was solved in order to verify the cross-over structure types and to ensure all possessed the same amount of hydration. Representations of the various structure types noted (Eu, La—OH, and Sc) are shown in FIGS. 1-3, respectively.

For the majority of lanthanides (Ce to Lu and Y), a dinuclear species was observed where each Ln possessed two terminal and two bridging hfip ligands. The Eu structure is shown in FIG. 1, as a representative of this structure type. The octahedral geometry (OC-6) around the metal center was finalized by coordinating two water molecules. These moieties were determined to be water molecules by several aspects of the final molecule: the Ln-O distance is within the range reported in the literature, protons were observed in several instances, and charge balance. The waters were found to be arranged cis to each other with numerous F—H interactions observed in the final structures.

For the Ln=La syntheses in eq. 1, numerous reaction attempts were undertaken but crystals proved difficult to isolate. As shown in FIG. 2(a), the compound isolated was La—OH, which proved to be a tetranuclear species, adopting a [La$_2$(μ$_3$-OH)]$_2$ central core. The protons were located on the hydroxides. The metals of La—OH were further bound together by an asymmetric binding of three μ-hfip ligands: two between La(2) and La(1A) and only one between La(2) and La(1). Each of the La possesses a terminal H$_2$O and H-hfip molecule. This adopts a cube-shared, corner missing arrangement, as shown in FIG. 2(b). This results in alternating pseudo octahedral geometry (OC-6) and 7-coordinated La metal centers; however, the F—La bonds push the coordination of each metal center one degree higher with 7- and 8-coordination geometries noted for La(2) and La(1), respectively.

Figure 4:
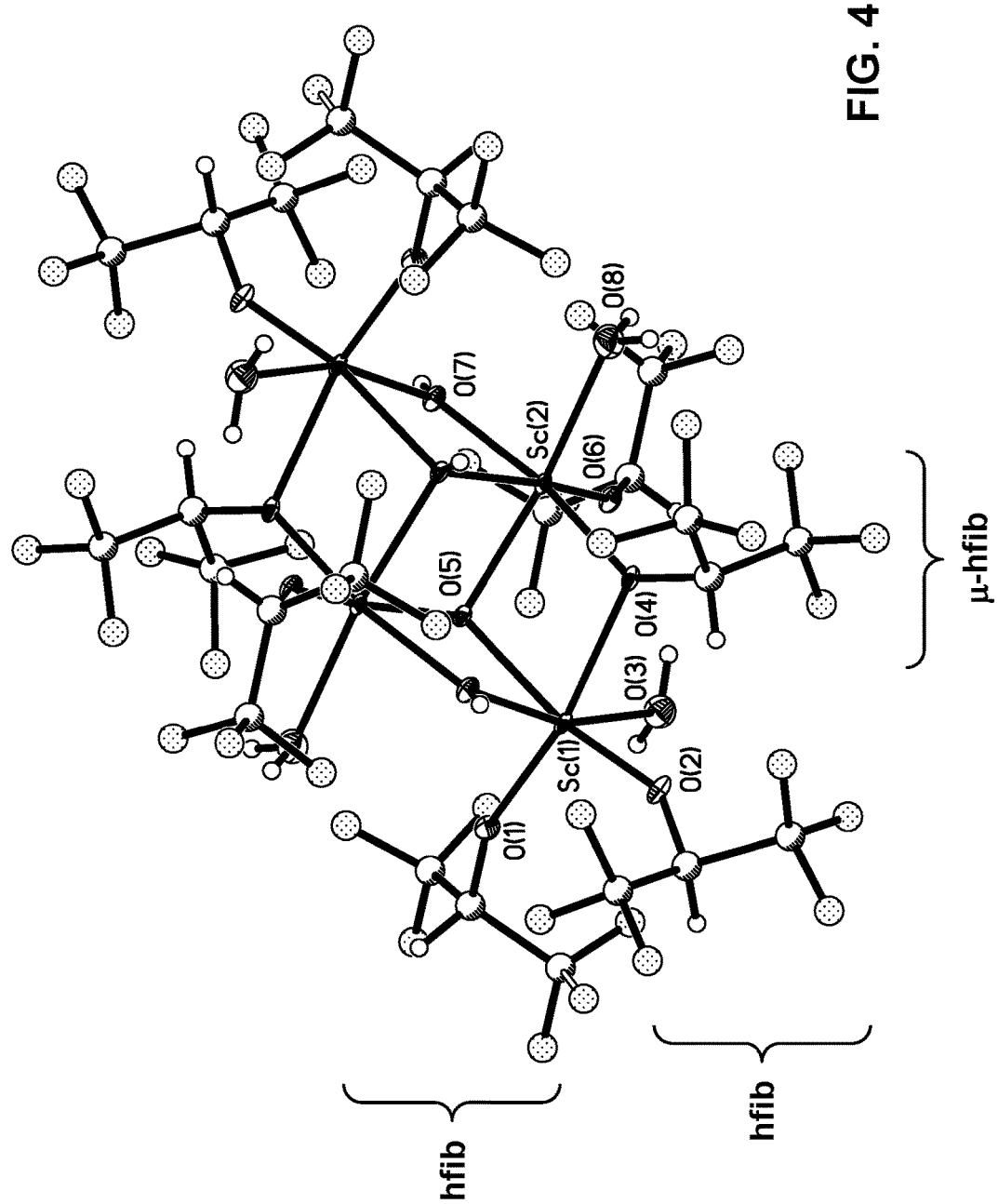
FIG. 4 is a structure plot of [$(H_2O)$(hfip)$_2$Sc($\mu$-hfip)($\mu$-OH)($\mu_3$-OH)Sc$(H_2O)$(hfip)]$_2$. Thermal ellipsoids of heavy atoms are drawn at 30%. Carbon, fluorine and hydrogen atoms are drawn as ball and stick for clarity.

The smallest cation, Sc, in this series was found to adopt a slightly different structure from the Ln derivatives mentioned above. While the species remained dinuclear with two hfip, two μ-hfip, and two water molecules bound to each metal, the variation in the structure of Sc was the trans arrangement of the water molecules in the axial position, as shown in FIG. 3. A separate synthesis on a larger scale at higher concentration with the remnants of an aged H-hfip reagent, led to the isolation of Sc—OH, as shown in FIG. 4. For this structure, each of the Sc metal centers is pseudo-CN-6, adopting a face-shared, corner-missing cube central core. Each of the terminal Sc atoms use one μ$_3$-OH, one μ-OH, one μ-hfip, one terminal H$_2$O and two terminal hfip ligands to fill their coordination sphere. The two interior Sc metal centers use the same ligand set with only one terminal hfip ligand. The structure is similar to that noted for La—OH but additional OH is present and no F—Sc interactions were readily noted. This structural change is most likely due to the smaller cation size and higher Lewis acidity of Sc versus La. It is not obvious at this point what led to the —OH formation. However, the increased concentration, high temperature, and potentially higher water content of the H-hfip may have contributed to the formation of this complex. Repetition of the reaction with fresh H-hfip, more toluene, and more controlled addition yielded Sc.

The adventitious water present in each of these compounds is thought to be from the H-hfip. Attempts to dehydrate the alcohol by storing it over molecular sieves proved fruitless as bound water was again located in all structures studied. Interestingly, the H$_2$O persists and is not converted to an oxide or hydroxide, except as noted for the Sc—OH and La—OH species. This is believed to be due to the H—F interactions and the pKa of the hfip ligand

[H—OCH(CH$_3$)$_2$ (16.5)>H—OH (15.7)>H—OCH(CF$_3$)$_2$ (9.3)]. The H-hfip ligand is a much weaker base than H$_2$O, so proton transfer cannot occur as it does in the non-fluorinated complexes.

Bulk Analysis.

Several different analyses were attempted to confirm the bulk powder compositions were consistent with the single crystal structures. The FTIR spectroscopy data previously discussed was in line with the final presence of hfip stretches, bends, and a broad stretch for the bound water around 3000 cm$^{-1}$. Complexometric titrations of the metal content of these compounds were undertaken. The % M present in the samples was found to be in-line with the calculated values of samples with no bound water.

NMR Spectroscopy.

As mentioned previously, the use of standard nuclei NMR is limited in probing the solution behavior of the bulk material since the majority of these compounds are paramagnetic. However, the Group 3 cations are accessible and some representative $^1$H, $^{13}$C, and $^{19}$F NMR data were collected using Sc and Y. If the structures were retained in solution the terminal and bridging (2:1 ratio) hfip ligands should yield: a $^1$H NMR spectrum with two septuplets split by the six F atom nearest neighbors and possible a singlet for the bound H—OH and H-hfip proton; a $^{13}$C{$^1$H} NMR spectrum with two sets of methine and methyl resonances; and a $^{19}$F spectrum with two singlets.

A variety of solvent systems (THF-d$_8$, py-d$_5$, CDCl$_3$, D$_2$O) were investigated for analysis of the solution behavior of these compounds. The low solubility of these compounds prevented in-depth analyses but CDCl$_3$ was ultimately found to be the best solvent that solubilizes the compounds and yielded meaningful spectral data. While a number of nuclei are available, the sensitive $^{19}$F (100% abundant, spin=½, receptivity relative to $^1$H=0.83, chemical shift range −300 to 400 ppm) proved to be a useful means for studying these compounds. The H-hfip ligand yielded a $^{19}$F shift at δ −76.9 ppm whereas each of the Ln-hfip species present a slightly shifted single resonance that is clustered around −75.8 ppm. To further study these compounds, solid state $^{19}$F spectra were collected on the same set of compounds. For each a single peak was noted at δ −77.1 (Sc) and −77.2 (Y). The difference in the chemical shift of the $^{19}$F resonances between the solid state and solution state indicates that the solution state structures are different from the single crystal X-ray structures. Possibly, this is a simple disruption of the dimer into monomeric species.

Nanomaterials

Representative samples were used to determine structure, cation, and solvation impact on the final nanomaterials generated. TGA data were collected on each of the compounds to determine their potential utility for conversion to LnF$_3$. Due to the similarity in structure of these compounds, the resulting spectra were expected to be very similar. A thermal exothermic event was noted for each sample around 250° C. The size of the event and sharpness of the peak varied with Lu being the broadest and Ce being the sharpest. All of the spectra have a small (5-7%) weight loss prior to 125° C., which is associated with loss of the two bound H$_2$O molecules. Two decomposition steps were noted for the majority of these samples, with a large weight loss before 400° C. The overall weight loss is much too small (~25-50%) to confirm complete conversion to either Sc$_2$O$_3$ or ScF$_3$. However, the temperature observed for the initial weight loss was consistent with successful solution routes to nanoparticles. Based on this data, two routes were used: (i) SOLVO and (ii) SPPT using amine solvents.

Solvothermal (SOLVO).

For the SOLVO route, two solvents were employed: pyridine (py) and trioctylamine (toa). Approximately 0.5 g of each sample was weighed out in a glovebox and added to ~40 mL of the selected solvent (py or toa) in a 60 mL digestion bomb. The bomb was sealed and transferred to an oven and heated to 185° C. for 12 h. After cooling to room temperature, in air, the insoluble material was isolated by centrifugation and washed several times with hexanes. Other The low boiling point py (115° C.) solvent was selected based on some oxide formation success in generating nanomaterials. The powders isolated were analyzed by PXRD; however, in each sample the peaks were very broad which made conclusive identification impossible. Therefore, high temperature crystallizations (450° C.) were undertaken by processing in a box furnace under circumjacent atmospheres. These processed powders were found to yield crystalline material, which were identified for: Ce as a mixture of cerianite (CeO$_2$) and fluocerite (CeF$_3$); Dy as dysprosium oxide fluoride (DyOF); and Y as a mixed phase of yttrium oxide fluoride and yttrium fluoride (YOF and YF$_3$). The lack of conversion was thought to be due to the low boiling point of py, so alternative higher boiling solvents were investigated under identical conditions. The selection of toa was based on the higher boiling point (164-168° C.) and the lone pair of electrons on the amine that could facilitate reduction. Samples run under similar conditions and processing when analyzed by PXRD were found to be: Ce (CeO$_2$ and CeF$_3$), Dy (DyO), and Lu (lutetium fluoride—LuF$_3$). For Y, olyelamine (ON; by 364° C.) was used as the solvent and the resulting sample appeared to be YF$_3$. Other high boiling point amines can also be used as solvents. Further, the SOLVO process can run as temperatures as low as about 150° C. for reaction times as short as about 6 hours.

Solution Precipitation (SPPT).

Due to the difficulty in isolating phase pure material for each sample by SOLVO routes, SPPT methods were also used.

SPPT could be operated at significantly higher temperatures (albeit lower pressures), which may facilitate uniform decomposition. Approximately 0.5 g of each sample was weighed out in the glovebox, brought out, and added to 50 mL Schlenk flask with oleylamine (ON, ~25 mL). The flask was fitted with a reflux condenser and nitrogen adaptor and the sample was heated to ~300° C. for 15-30 min under a stream of flowing argon. After cooling to room temperature, the reaction mixture was transferred to a glovebox and the reaction mixture was washed several times with hexanes and the precipitate collected by centrifugation. Lower temperatures (e.g., 280° C.) and longer reaction times can also be used.

The phases noted for these samples were identified as: Ce led to phase pure CeF$_3$; Tb formed terbium fluoride (TbF$_3$); Dy yielded DyOF; Yb mixture of Yb(O,F)$_{1.93}$ and YbF$_2$; Y produced a mixture of YOF, Y$_5$O$_4$F$_7$ and YF$_3$; Sc formed a mixture of Sc$_2$O$_3$ and ScF$_3$.

The present invention has been described as a method to synthesize lanthanide fluoride materials from lanthanide fluorinated alkoxides. It will be understood that the above description is merely illustrative of the applications of the principles of the present invention, the scope of which is to be determined by the claims viewed in light of the specification. Other variants and modifications of the invention will be apparent to those of skill in the art.

TABLE 1(a)

Data collection parameters for Ce-Gd.

| Compound | Ce | Pr | Nd | Eu | Gd |
|---|---|---|---|---|---|
| chemical formula | $C_{18}H_{14}Ce_2F_{36}O_{10}$ | $C_{18}H_{14}F_{36}O_{10}Pr_2$ | $C_{18}H_{14}F_{36}Nd_2O_0$ | $C_{36}H_{24}Eu_4F_{72}O_{28}$ | $C_{18}H_{14}F_{36}Gd_2O_{10}$ |
| formula weight | 1354.53 | 1356.11 | 1362.77 | 2752.39 | 1388.79 |
| temp (K) | 100.0 (2) | 100.0 (2) | 100.0 (2) | 100.0 (2) | 100.0 (2) |
| space group | Orthorhombic $Pca2_1$ | Orthorhombic $Pca2_1$ | Triclinic $P(-1)$ | Triclinic $P(-1)$ | Triclinic $P(-1)$ |
| a (Å) | 16.4521 (15) | 16.3868 (7) | 10.2439 (10) | 10.3651 (5) | 10.3623 (6) |
| b (Å) | 12.1757 (11) | 12.2136 (10) | 12.3405 (12) | 12.3507 (6) | 12.3298 (8) |
| c (Å) | 19.8324 (18) | 19.7212 (12) | 16.2956 (17) | 16.4380 (8) | 16.4569 (10) |
| α (deg) | | | 93.405 (4) | 93.571 (2) | 93.688 (2) |
| β (deg) | | | 99.087 (4) | 99.646 (2) | 99.674 (2) |
| γ (deg) | | | 108.640 (4) | 108.610 (2) | 108.576 (2) |
| V (Å$^3$) | 3972.7 (6) | 3947.0 (4) | 1914.1 (3) | 1950.96 (17) | 1949.0 (2) |
| Z | 4 | 4 | 2 | 1 | 2 |
| $D_{calcd}$(Mg/m$^3$) | 2.265 | 2.282 | 2.364 | 2.343 | 2.366 |
| μ, (Mo, Kα) (mm$^{-1}$) | 2.476 | 2.655 | 2.904 | 3.03 | 3.591 |
| R1$^a$ (%) (all data) | 2.14 (2.38) | 2.51 (2.68) | 5.02 (11.34) | 2.12 (2.48) | 5.41 (6.85) |
| wR2$^b$ (%) (all data) | 4.92 (5.04) | 6.32 (6.48) | 9.47 (11.53) | 5.31 (5.59) | 15.02 (16.47) |

TABLE 1(b)

Data collection parameters for Tb-Tm.

| Compound | Tb | Dy | Ho | Er | Tm |
|---|---|---|---|---|---|
| chemical formula | $C_{18}H_{11}F_{36}O_{10}Tb_2$ | $C_{18}H_{14}Dy_2F_{36}O_{10}$ | $C_{18}H_6F_{36}HO_2O_{10}$ | $C_{36}H_{26}Er_2F_{72}O_{20}$ | $C_9H_7F_{18}O_5Tm$ |
| formula weight | 1389.11 | 1399.29 | 1396.09 | 2815.61 | 706.08 |
| temp (K) | 100.0 (2) | 100.0 (2) | 100.0 (2) | 100.0 (2) | 100.0 (2) |
| space group | Triclinic $P(-1)$ | Triclinic $P(-1)$ | Triclinic $P(-1)$ | Triclinic $P(-1)$ | Triclinic $P(-1)$ |
| a (Å) | 10.3565 (5) | 10.3508 (5) | 10.3413 (5) | 10.3447 (6) | 10.3263 (15) |
| b (Å) | 12.3041 (6) | 12.2871 (5) | 12.2700 (6) | 12.2525 (7) | 12.2572 (18) |
| c (Å) | 16.4125 (8) | 16.4262 (8) | 16.4064 (8) | 16.3492 (9) | 16.370 (2) |
| α (deg) | 93.538 (2) | 93.668 (2) | 93.693 (2) | 93.685 (3) | 93.602 (4) |
| β (deg) | 100.103 (2) | 100.074 (2) | 100.112 (2) | 100.937 (3) | 100.535 (4) |
| γ (deg) | 108.192 (2) | 108.362 (2) | 108.295 (2) | 107.106 (3) | 107.713 (4) |
| V (Å$^3$) | 1940.83 (17) | 1936.26 (16) | 1929.87 (16) | 1928.60 (19) | 1924.9 (5) |
| Z | 2 | 2 | 2 | 1 | 4 |
| $D_{calcd}$(Mg/m$^3$) | 2.377 | 2.400 | 2.396 | 2.424 | 2.436 |
| μ, (Mo, Kα) (mm$^{-1}$) | 3.833 | 4.049 | 4.289 | 4.542 | 4.800 |
| R1$^a$ (%) (all data) | 2.23 (2.94) | 4.32 (7.01) | 3.89 (5.08) | 2.14 (2.27) | 2.29 (2.93) |
| wR2$^b$ (%) (all data) | 5.32 (5.70) | 8.54 (9.47) | 9.90 (11.18) | 5.50 (5.60) | 4.92 (5.19) |

TABLE 1(c)

Data collection parameters for Yb-Sc.

| Compound | Yb | Lu | Y | Sc |
|---|---|---|---|---|
| chemical formula | $C_{18}H_{14}F_{36}O_{10}Yb_2$ | $C_{18}H_{14}F_{36}Lu_2O_{10}$ | $C_{36}H_{26}F_{72}O_{20}Y_4$ | $C_{18}H_{14}F_{36}O_{10}Sc_2$ |
| formula weight | 1420.37 | 1424.23 | 2502.21 | 1164.21 |
| temp (K) | 100.0 (2) | 100.0 (2) | 100.0 (2) | 100.0 (2) |
| space group | Triclinic $P(-1)$ | Triclinic $P(-1)$ | Triclinic $P(-1)$ | Monoclinic $P21/n$ |
| a (Å) | 10.3255 (4) | 10.2923 (8) | 10.3637 (8) | 9.8165*5 ( |
| b (Å) | 12.2523 (5) | 11.2778 (9) | 12.2784 (10) | 14.1388 (7) |
| c (Å) | 16.3105 (6) | 11.3676 (9) | 16.3853 (12) | 14.2433 (7) |
| α (deg) | 93.5990 (10) | 112.727 (2) | 93.688 (3) | |
| β (deg) | 101.0720 (10) | 94.305 (2) | 100.708 (3) | 100.225 (2) |
| γ (deg) | 107.3230 (10) | 110.302 (2) | 107.554 (3) | |
| V (Å$^3$) | 1917.29 (13) | 1107.58 | 1937.2 (3) | 1945.48 (17) |
| Z | 2 | 1 | 1 | 2 |
| $D_{calcd}$(Mg/m$^3$) | 2.460 | 2.135 | 2.145 | 1.987 |
| μ, (Mo, Kα) (mm$^{-1}$) | 5.069 | 4.622 | 3.200 | 0.567 |
| R1$^a$ (%) (all data) | 2.32 (2.76) | 2.37 (2.73) | 5.62 (8.64) | 3.66 (4.70) |
| wR2$^b$ (%) (all data) | 5.20 (5.43) | 5.12 (5.41) | 13.42 (17.71) | 8.87 (9.54) |

$^a$R1 = Σ | |F$_o$| − |F$_c$| |/Σ |F$_o$| × 100
$^b$wR2 = [Σ w (F$_o^2$ − F$_c^2$)$^2$/Σ (w |F$_o$|$^2$)$^2$]$^{1/2}$ × 100

I claim:

1. A method to synthesize lanthanide fluoride nanoparticles, comprising reacting hexafluoro iso-propanol with [Ln(NR$_2$)$_3$], where R=Si(CH$_3$)$_3$ and Ln=La, Ce, Pr, Nd, Sm, Eu, Gd, Tb, Dy, Ho, Er, Tm Yb, Lu, Y, or Sc, in a first organic solvent to form a lanthanide hexafluoro iso-propoxide derivative and adding the lanthanide hexafluoro iso-propoxide derivative to a second organic solvent and solvothermal processing the solution at a sufficiently high temperature and pressure to produce lanthanide fluoride nanoparticles.

2. The method of claim 1, wherein the second organic solvent comprises a high boiling point amine.

3. The method of claim 2, wherein the second organic solvent comprises trioctylamine.

4. The method of claim 2, wherein the second organic solvent comprises pyridine.

5. The method of claim 1, wherein the temperature is greater than 150° C.

6. A method to synthesize lanthanide fluoride nanoparticles, comprising reacting hexafluoro iso-propanol with [Ln(NR$_2$)$_3$], where R=Si(CH$_3$)$_3$ and Ln=La, Ce, Pr, Nd, Sm, Eu, Gd, Tb, Dv, Ho, Er, Tm, Yb, Lu, Y, or Sc, in a first organic solvent to form a lanthanide hexafluoro iso-propoxide derivative and adding the lanthanide hexafluoro iso-propoxide derivative to a second organic solvent and heating the solution at a sufficiently high temperature to precipitate lanthanide fluoride nanoparticles.

7. The method of claim 6, wherein the second organic solvent comprises oleylamine or hexadecylamine.

8. The method of claim 6, wherein the temperature is greater than 280° C.

9. The method of claim 6, wherein the first organic solvent comprises a non-polar solvent.

10. The method of claim 6, wherein the first organic solvent comprises toluene.

11. The method of claim 6, wherein the first organic solvent comprises hexane.

12. The method of claim 1, wherein the first organic solvent comprises a non-polar solvent.

13. The method of claim 1, wherein the first organic solvent comprises toluene.

14. The method of claim 1, wherein the first organic solvent comprises hexane.

* * * * *